(12) United States Patent
Shigemitsu et al.

(10) Patent No.: US 11,187,674 B2
(45) Date of Patent: Nov. 30, 2021

(54) ANALYTICAL TOOL AND ANALYTICAL SYSTEM

(71) Applicant: ARKRAY, Inc., Kyoto (JP)

(72) Inventors: Takanari Shigemitsu, Kyoto (JP); Naotsugu Onuma, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 380 days.

(21) Appl. No.: 15/373,911

(22) Filed: Dec. 9, 2016

(65) Prior Publication Data

US 2017/0168013 A1    Jun. 15, 2017

(30) Foreign Application Priority Data

Dec. 9, 2015   (JP) ............................. JP2015-239915
Nov. 8, 2016   (JP) ............................. JP2016-217921

(51) Int. Cl.
*G01N 27/447*       (2006.01)
*B01L 3/00*         (2006.01)
(Continued)

(52) U.S. Cl.
CPC .... *G01N 27/44791* (2013.01); *B01L 3/50273* (2013.01); *B01L 3/502715* (2013.01);
(Continued)

(58) Field of Classification Search
CPC ........................ G01N 27/447–27/44752; G01N 27/44756–27/453; B01L 2400/0421; B01L 2400/0487; B01L 3/50273; B01L 3/502715; B01L 2200/0689; B01L 2300/0645; B01L 2300/0681; B01L 2300/0816; B81B 1/00–1/008
See application file for complete search history.

(56) References Cited

U.S. PATENT DOCUMENTS 5,599,433 A     2/1997  Keo et al.
6,086,825 A *   7/2000  Sundberg ............ B01J 19/0093
                                              204/600
(Continued)

FOREIGN PATENT DOCUMENTS

GB      2439233 A      12/2007
JP      1997-510792 A  10/1997
(Continued)

OTHER PUBLICATIONS

English Machine Translation of Koike et al. (JP1133027) (Year: 1999).*

(Continued)

*Primary Examiner* — Maris R Kessel
(74) *Attorney, Agent, or Firm* — Morgan, Lewis & Bockius LLP (57) ABSTRACT

An analytical tool is provided for analysis of a sample by capillary electrophoresis. The analytical tool includes an inlet reservoir into which a sample is introduced, a capillary tube in communication with the inlet reservoir, a filter through which a liquid from the inlet reservoir passes, an enlarged portion undergoing a sudden increase in a cross-sectional area and being in communication with the inlet reservoir and the capillary tube, and a pressure fluctuation reducer for preventing pressure fluctuation at the enlarge portion from affecting a liquid in the capillary tube.

12 Claims, 10 Drawing Sheets

(51) Int. Cl.
*G01N 33/49* (2006.01)
*G01N 33/487* (2006.01)

(52) U.S. Cl.
CPC . *G01N 27/44704* (2013.01); *G01N 33/48707* (2013.01); *G01N 33/49* (2013.01); *G01N 33/491* (2013.01); *B01L 2200/0689* (2013.01); *B01L 2300/0645* (2013.01); *B01L 2300/0681* (2013.01); *B01L 2300/0816* (2013.01); *B01L 2400/0487* (2013.01)

(56) References Cited

U.S. PATENT DOCUMENTS

| | | | |
|---|---|---|---|
| 6,111,096 A | 8/2000 | Laugharn | |
| 2002/0025576 A1* | 2/2002 | Northrup | G01N 27/44743 435/288.5 |
| 2002/0144907 A1* | 10/2002 | Yamamoto | G01N 27/44791 204/453 |
| 2005/0148091 A1* | 7/2005 | Kitaguchi | B01L 3/502723 436/164 |
| 2006/0018790 A1* | 1/2006 | Naka | G01N 21/03 422/400 |
| 2006/0102478 A1 | 5/2006 | Robert et al. | |
| 2010/0032294 A1 | 2/2010 | Nakayama et al. | |
| 2010/0116660 A1 | 5/2010 | Tanaka et al. | |
| 2010/0258440 A1 | 10/2010 | Sugiyama et al. | |
| 2012/0245042 A1* | 9/2012 | Liu | C12M 23/16 506/7 |
| 2015/0209783 A1* | 7/2015 | Ingber | C12M 23/16 435/297.1 |

FOREIGN PATENT DOCUMENTS

| | | | |
|---|---|---|---|
| JP | 11133027 A | * | 5/1999 |
| JP | H11-133027 A | | 5/1999 |
| JP | 2006-145537 A | | 6/2006 |
| JP | 2009-109230 A | | 5/2009 |
| JP | 2014-190719 A | | 10/2014 |
| JP | 2014190719 A | * | 10/2014 |
| WO | WO 98/55852 A1 | | 12/1998 |
| WO | WO 99/22868 A1 | | 5/1999 |
| WO | WO 2008/136321 A1 | | 11/2008 |
| WO | WO 2008/136465 A1 | | 11/2008 |
| WO | WO 2010/010859 A1 | | 1/2010 |

OTHER PUBLICATIONS

English Machine Translation of JP-2014190719-A.*
European Search Report dated Apr. 12, 2017, received in European Patent Application No. 16202377.4.
Japanese Office Action dated Jul. 30, 2019 issued in corresponding Japanese Patent Application No. 2016-217921 along with machine translation of same.
Office Action issued in corresponding European Patent Application No. 16202377.4 dated Apr. 28, 2020.
Office Action dated Dec. 11, 2019 in corresponding European Patent Application No. 16 202 377.4 in English.
Office Action issued in related European Patent Application No. 16202377.4 dated Feb. 15, 2021.

* cited by examiner

ANALYTICAL TOOL AND ANALYTICAL SYSTEM

BACKGROUND OF THE INVENTION

1. Field of the Invention

The present invention relates to analytical tools and analytical systems.

2. Description of the Related Art

The degrees of glycation of various proteins have been analyzed and used as indicators showing the state of a living body. Among such indicators, the glycation degree of hemoglobin (Hb) in general, and of stable HbA1c (hereinafter, may be referred to simply as "s-HbA1c") in particular, reflects the past history of the blood glucose level in a living body and thus serves as an important indicator in, for example, the diagnosis and treatment of diabetes. HbA1c is defined as HbA ($\alpha 2\beta 2$) glycated at the N-terminal valine of the $\beta$ chain.

Electrophoresis is used as an analytical technique for Hb, particularly for s-HbA1c. For example, JP-A-2006-145537, JP-A-H9-510792, WO 2010/010859, JP-A-2009-109230, WO 2008/136321 and WO 2008/136465 teach adding an additional component to a buffer solution with the aim of optimizing analysis and improving the accuracy. Specifically, JP-A-2009-109230 and WO 2008/136321 teach chondroitin sulfate as an example of an additional component of the buffer solution. In addition, WO 2008/136465 describes an analytical process involving supplying a sample continuously during electrophoretic separation of the sample. Such a method facilitates an electrophoresis chip used in the method to be more compact.

A typical sample to be analyzed is blood, which is a biological sample. Naturally, blood collected as a sample from a patient may have various properties depending on the patient's conditions, including the disease state and the physical make-up. In addition, the additional components and/or analytical processes cited above may result in creation of substances potentially interfering with proper analysis but not much has been revealed. The same applies to analysis on samples other than blood. To improve the accuracy of analysis, removing such interfering substances is preferable. However, removal of such interfering substances may affect the electrophoresis in a capillary tube.

SUMMARY OF THE INVENTION

In view of the circumstances described above, the present invention aims to provide an analytical tool and an analytical system capable of performing proper analysis.

According to a first aspect of the present invention, there is provided an analytical tool for analysis of a sample by capillary electrophoresis. In an embodiment, the analytical tool is provided with: an inlet reservoir into which a sample is introduced; a capillary tube in communication with the inlet reservoir; a filter through which a liquid from the inlet reservoir passes; an enlarged portion undergoing a sudden increase in a cross-sectional area and being in communication with the inlet reservoir and the capillary tube; and a pressure fluctuation reducer for preventing pressure fluctuation at the enlarge portion from affecting a liquid in the capillary tube.

Preferably, the analytical tool may further include a secondary reservoir provided with the enlarged portion.

Preferably, the analytical tool may further include a connection channel connecting the inlet reservoir to the enlarged portion, where the capillary tube is in communication with the connection channel at a location between the inlet reservoir and the enlarged portion.

Preferably, the pressure fluctuation reducer may include a flat member covering at least a part of the enlarged portion and allowing gas flow.

Preferably, the pressure fluctuation reducer may have a portion fixed to the enlarged portion.

Preferably, the pressure fluctuation reducer may be made of a liquid-impermeable resin.

Preferably, the flat member may have a hydrophilic surface facing the enlarged portion.

Preferably, the pressure fluctuation reducer may be made of a liquid-permeable porous material.

Preferably, the pressure fluctuation reducer may include a hydrophilic region formed by an inner surface region of the enlarged portion treated to be hydrophilic.

Preferably, the pressure fluctuation reducer may include an open reservoir that is in communication with the secondary reservoir through the connection channel.

Preferably, the secondary reservoir may be separated from the open reservoir.

Preferably, the secondary reservoir may be continuous with the open reservoir.

Preferably, the analytical tool may be configured as a disposable tool.

According to a second aspect of the present invention, there is provided an analytical system that includes: an analytical tool noted above; and an analyzing unit into which the analytical tool is installed and configured to perform analysis by capillary electrophoresis in the capillary tube.

According to the present invention, the pressure fluctuation reducer ensures that the liquid reaching the enlarged portion will not have surface tension which would cause pressure fluctuations in the capillary tube. As a result, unintentional migration of the liquid in the capillary tube is prevented. The analytical tool and system of the present invention are capable of removing interfering substances and yet capable of more stable analysis.

Other features and advantages of the present invention will become more apparent from the detailed description given below with reference to the accompanying drawings.

DETAILED DESCRIPTION OF THE PREFERRED EMBODIMENTS

Preferred embodiments of the present invention will now be specifically described with reference to the accompanying drawings.

Figure 1:
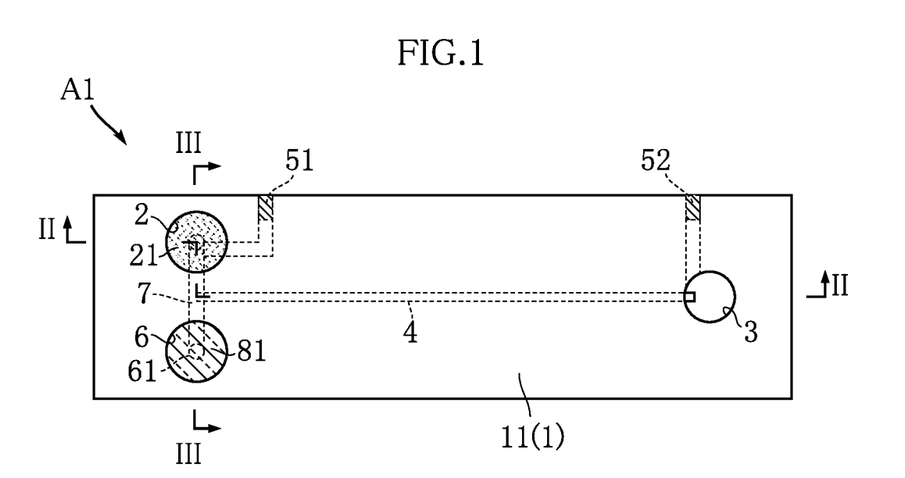
FIG. 1 is a plan view of an analytical tool according to Embodiment 1 of the present invention.
Figure 2:
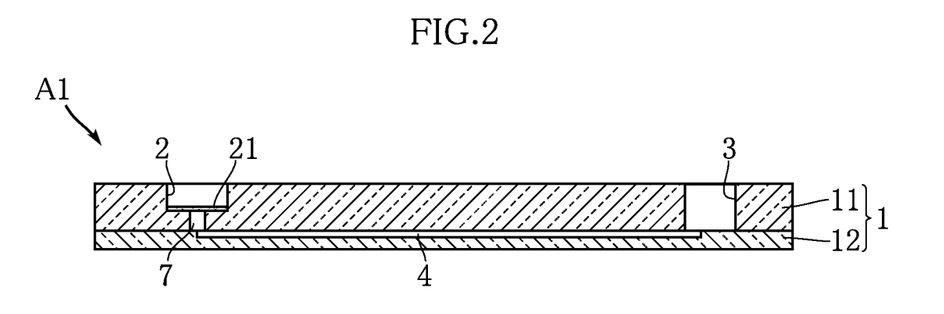
FIG. 2 is a cross-sectional view taken along line II-II of FIG. 1.
Figure 3:
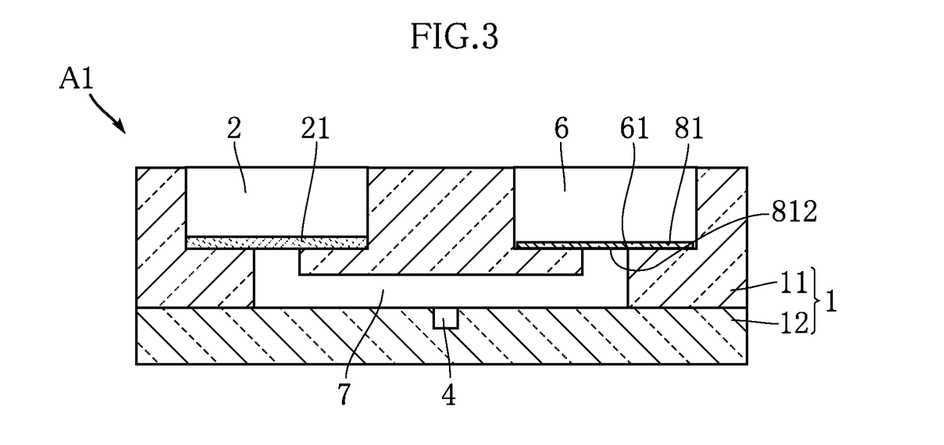
FIG. 3 is a cross-sectional view taken along line III-III of FIG. 1.
Figure 4:
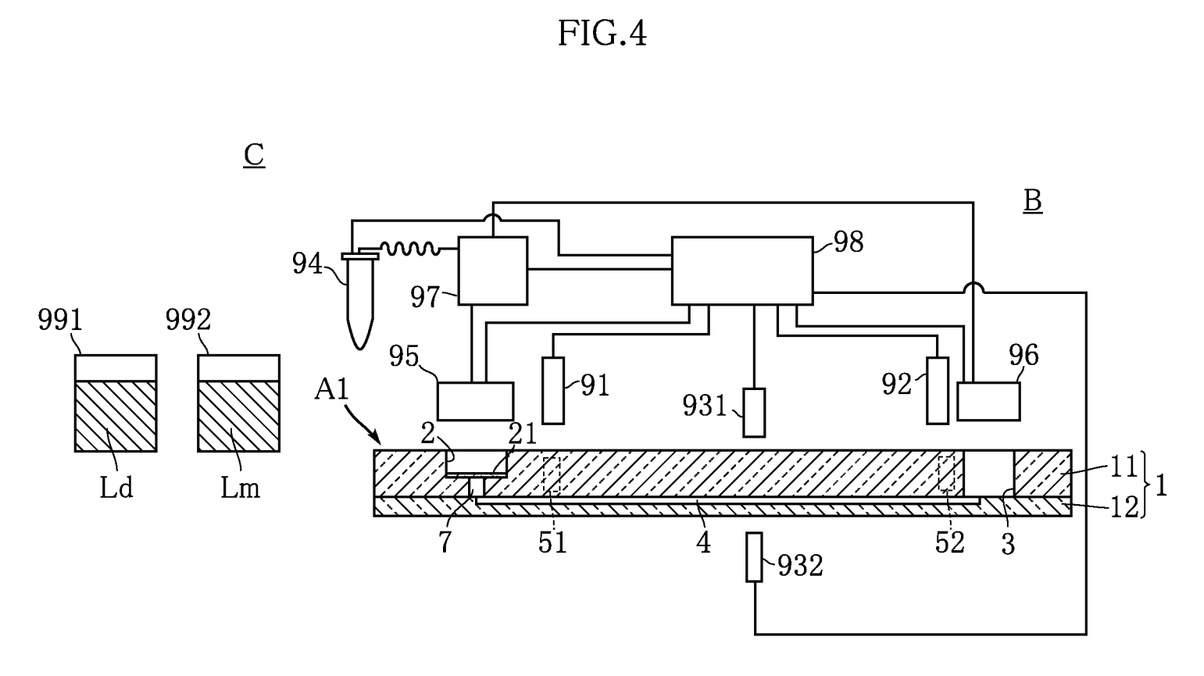
FIG. 4 is a block diagram showing an analytical system according to Embodiment 1 of the present invention.

FIGS. 1 to 3 show an analytical tool according to Embodiment 1 of the present invention. FIG. 4 shows an analytical system according to Embodiment 1 of the present invention. An analytical system C of this embodiment includes an analytical device B and an analytical tool A1. The analytical system C performs an analytical process on a sample by using electrophoresis. Samples to be analyzed are not particularly limited. In this embodiment, the samples are blood collected from human subjects. Among the components of a sample, those targeted for analysis are defined as analyte components.

Examples of the analyte components include hemoglobin (Hb), albumin (Alb), globulin ($\alpha 1$, $\alpha 2$, $\beta$, and $\gamma$ globulins) and fibrinogen. Examples of hemoglobin include normal hemoglobin (HbA0), glycated hemoglobin, modified hemoglobin and fetal hemoglobin (HbF). Examples of glycated hemoglobin include hemoglobin A1a (HbA1a), hemoglobin A1b (HbA1b), hemoglobin A1c (HbA1c) and GHbLys. Examples of hemoglobin A1c include stable HbA1c (s-HbA1c) and unstable HbA1c. Examples of modified hemoglobin include carbamylated Hb and acetylated Hb.

The analytical tool A1 is installed into the analytical device B to provide a site for analysis. In this embodiment, the analytical tool A1 is a disposable analytical chip, which is designed to be used once or a limited number of times and then disposed. As shown in FIGS. 1 to 3, the analytical tool A1 includes a body 1, an inlet reservoir 2, a filter 21, an outlet reservoir 3, a capillary tube 4, electrode contact elements 51 and 52, a secondary reservoir 6, a connection channel 7 and a flat member 81. FIG. 1 is a plan view of the analytical tool A1. FIG. 2 is a cross-sectional view taken along line II-II of FIG. 1. FIG. 3 is a cross-sectional view taken along line of FIG. 1.

The body 1 is a base of the analytical tool A1 and made of a material that is not particularly limited. Examples of materials for the body 1 include glass, fused silica and plastic. In this embodiment, the body 1 includes an upper base 11 and a lower base 12 jointed together. Alternatively, the body 1 may be constructed of a single piece.

The inlet reservoir 2 servers as an inlet for introducing a solution containing a sample. In this embodiment, the inlet reservoir 2 is formed in the upper base 11 of the body 1. In one example, the sample-containing solution may be a diluted sample prepared by diluting a sample such as blood with a predetermined diluent. The dilution may be performed in another reservoir (not shown) of the analytical tool A1 or in the analytical device B, which will be described later.

The filter 21 is disposed such that a solution introduced into the inlet reservoir 2 flows through for removing interfering substances, examples of which are listed below. In this embodiment, the filter 21 is disposed on the bottom of the inlet reservoir 2. The filter 21 is not limited to any specific configuration as long as interfering substances can be appropriately removed. A cellulose acetate membrane filter (available from ADVANTEC, Type: Y100, Thickness: 95 µm) is one preferable example.

The outlet reservoir 3 is disposed at a downstream end of an electroosmotic flow in capillary electrophoresis. The outlet reservoir 3 may be a through hole formed in the upper base 11 of the body 1.

The capillary tube 4 connects the inlet reservoir 2 and the outlet reservoir 3, and an electroosmotic flow occurs through the capillary tube 4. The capillary tube 4 may be a groove formed in the lower base 12 of the body 1. The body 1 may have recesses or similar structure through which light can travel toward the capillary tube 4 and exit after passing through the capillary tube 4. The capillary tube 4 is not limited to any particular size and may, for example, be 25 to 100 µm in width, 25 to 100 µm in height or depth, and 5 to 150 mm in length. The overall size of the analytical tool A1 is determined depending on the size of the capillary tube 4 as well as the sizes and arrangements of the inlet reservoir 2, the outlet reservoir 3, the secondary reservoir 6, and so on.

The electrode contact elements 51 and 52 are used for establishing electrical connection with the analytical device B. When electrical connection is established, a voltage is applied to the capillary tube 4 for causing electrophoresis. The electrode contact element 51 and the inlet reservoir 2 are on the same side of the capillary tube 4. The electrode contact element 52 and the outlet reservoir 3 are on the same side of the capillary tube 4. The electrode contact elements 51 and 52 are not limited to any specific configuration and can be any elements for establishing electrical connection to the analytical device B and applying a voltage to a liquid in the capillary tube 4. This embodiment is directed to an example in which the electrode contact elements 51 and 52 are metallic pipes disposed as channels. The channel of the electrode contact element 51 is in communication with the inlet reservoir 2, whereas the channel of the electrode contact element 52 is in communication with the outlet reservoir 3. Electrical connection is established when the electrodes (not shown) or other parts of the analytical device B are placed in contact with the outer surface of each metallic pipe, while a liquid is in contact with its inner surface of the pipe. In an alternative example, the electrode contact elements 51 and 52 may be reservoirs for holding a liquid. In this case, electrical connection is established when the electrodes (not shown) or other parts of the analytical device B are put into the liquid.

The secondary reservoir 6 has an enlarged portion 61 and is in communication with the inlet reservoir 2 and the capillary tube 4. In this embodiment, the secondary reservoir 6 is formed in the upper base 11 of the body 1. The interior of the secondary reservoir 6 from the enlarged portion 61 to its top opening has a cross-sectional area that is substantially larger than the connection channel 7. Therefore, the enlarged portion 61 provides a sudden increase in the cross-sectional area of the flow passage. Note that the "sudden increase" in the cross-sectional area of the flow passage refers to an increase such that a liquid surface at the enlarged portion 61 will have a surface tension which may affect migration of the liquid in the capillary tube 4 during a later-described analytical process.

The connection channel 7 provides a flow passage between the inlet reservoir 2 and the secondary reservoir 6. In this embodiment, the connection channel 7 is a groove formed in the upper base 11 of the body 1. The capillary tube 4 is connected to the connection channel 7 at a location between the inlet reservoir 2 and the outlet reservoir 3.

The flat member 81 is an example of a pressure fluctuation reducer. The pressure fluctuation reducer serves to reduce pressure fluctuations in a liquid within the capillary tube 4 caused in the presence of surface tension of the liquid at the enlarged portion 61. In this embodiment, the flat member 81 is a planer member disposed to have a thickness in a direction coinciding with the depth direction of the secondary reservoir 6. In this embodiment, the flat member 81 is made of a resin having liquid impermeability. One example of such a resin is PET resin. In this embodiment, the flat member 81 is made of a PET film (available from FUJIMORI KOGYO, Type: TCP188, Thickness: 188 μm). In this embodiment, the flat member 81 is placed in the secondary reservoir 6 so as to close the connection channel 7 but is not fixed or bonded to the secondary reservoir 6.

In addition, the flat member 81 of this embodiment has a hydrophilic surface 812. The hydrophilic surface 812 is formed by treating a surface of the flat member 81 to be hydrophilic. The hydrophilic surface 812 faces the enlarged portion 61.

The analytical device B performs analysis by electrophoresis, with the analytical tool A1 installed in the analytical device B. The analytical device B includes electrodes 91 and 92, a light emitting unit 931, a light receiving unit 932, an inlet nozzle 94, pressure nozzles 95 and 96, a pump 97, a controller 98, a diluent reservoir 991 and a buffer reservoir 992. For convenience, FIG. 4 illustrates the components of the analytical device B only schematically.

The electrodes 91 and 92 are used to apply a predetermined voltage across the capillary tube 4 for causing electrophoresis. In this embodiment, the electrode 91 is brought into contact with the electrode contact element 51 of the analytical tool A1, and the electrode 92 with the electrode contact element 52 of the analytical tool A1 to apply a voltage. The magnitude of a voltage applied across the electrodes 91 and 92 is not particularly limited and may be within a range of 0.5 to 20 kV. In one example, the electrodes 91 and 92 are configured to be movable toward and away from the analytical tool A1 in a predetermined direction.

The light emitting unit 931 emits light for measuring absorbance in electrophoresis analysis. The light emitting unit 931 includes a light-emitting element such as an LED chip for emitting light in a predetermined wavelength range, an optical filter and a lens. The optical filter passes certain wavelengths of light emitted from the light-emitting element, while attenuating other wavelengths. The lens is used to converge light having passed through the optical filter to a specific analysis point in the capillary tube 4 of the analytical tool A1. The light emitting unit 931 may be provided with one or more slits to remove undesirable components which may scatter, from light traveled through the optical filter and the lens.

The light receiving unit 932 receives light traveled through the analysis point in the capillary tube 4 of the analytical tool A1 and includes, for example, a photodiode and a photo IC.

The diluent reservoir 991 holds a diluent Ld used to dilute the sample to a concentration appropriate for the analysis. In this embodiment, the diluent Ld contains an additional component (described later) for enabling removal interfering substances. The main component of the diluent Ld is not particularly limited and may be water or saline, for example. Preferably, the main component of the diluent Ld is similar in composition to a buffer solution Lm, which will be described below. The diluent Ld contains, as the additional component mentioned above, an anionic group-containing compound added to the main component. Examples of anionic group-containing compounds include an anionic group-containing polysaccharide. The anionic group-containing polysaccharide may be at least one polysaccharide selected from the group consisting of sulfated polysaccharide, carboxylated polysaccharide, sulfonated polysaccharide and phosphorylated polysaccharide. The carboxylated polysaccharide is preferably alginic acid or a salt thereof (such as sodium alginate). The sulfated polysaccharide may be chondroitin sulfate. There are seven types of chondroitin sulfates A, B, C, D, E, H and K, and any of them may be used. In the flowing description, the diluent Ld is prepared by adding chondroitin sulfate to the main component having the same composition as the buffer solution Lm. In one example, the anionic group-containing compound (chondroitin sulfate) is contained in a concentration of, for example, 0.01% to 5% by weight.

The buffer reservoir 992 holds the buffer solution Lm. The buffer solution Lm is introduced into e.g., the capillary tube 4 to provide a site for capillary electrophoresis. Although the buffer solution Lm is not particularly limited, one containing an acid is preferable. Examples of acids include citric acid, maleic acid, tartaric acid, succinic acid, fumaric acid, phthalic acid, malonic acid and malic acid. Preferably, the buffer solution Lm contains a weak base. Examples of weak bases include arginine, lysine, histidine and tris. In one example, the buffer solution Lm has a pH of 4.5 to 6. The buffer solution Lm may be any of MES, ADA, ACES, BES, MOPS, TES, HEPES, and so on. The buffer solution Lm contains an anionic group-containing compound, which is also contained in the diluent Ld. In one example, the anionic group-containing compound (chondroitin sulfate) is contained in a concentration of 0.01% to 5% by weight.

In the analytical system according to the present invention, reservoirs for holding the diluent Ld and the buffer solution Lm may be disposed in the analytical tool A1. In addition, a reservoir for mixing a sample such as blood with the diluent Ld may be disposed either in the analytical tool A1 or in the analytical device B.

The inlet nozzle 94 is used to suck up the diluent Ld from the diluent reservoir 991, the buffer solution Lm from the buffer reservoir 992, and the diluted sample from the mixing reservoir (not shown) and introduce into appropriate parts of the analytical tool A1.

The pressure nozzle 95 applies a predetermined pressure (negative or positive pressure) to the inlet reservoir 2 of the analytical tool A1 when placed in close proximity to the inlet reservoir 2. The pressure nozzle 96 applies a predetermined pressure (negative or positive pressure) to the outlet reservoir 3 of the analytical tool A1 when in when placed in close proximity to the outlet reservoir 3.

The pump 97 is connected to the inlet nozzle 94, the pressure nozzle 95 and the pressure nozzle 96, and acts as a pressure source used to apply pressure to the inlet nozzle 94, the pressure nozzle 95 and the pressure nozzle 96. The pump 97 may be additionally connected to the pressure nozzle (not shown) for applying pressure from a location within the analytical tool A1, other than from the inlet nozzle 94, the pressure nozzle 95 and the pressure nozzle 96.

The controller 98 controls the parts and units of the analytical device B. The controller 98 may include a CPU, memory and interface.

The following now describes an analytical process performed using the analytical system C (analytical tool A1). The analytical process may include a sample collecting step, a buffer introducing step, a mixing step and an electrophoresis step.

<Sample Collecting Step>

First, a sample is prepared. In this embodiment, the sample is blood collected from a human body. The blood sample may be whole blood or blood after hemolysis.

<Buffer Introducing Step>

Figure 5:
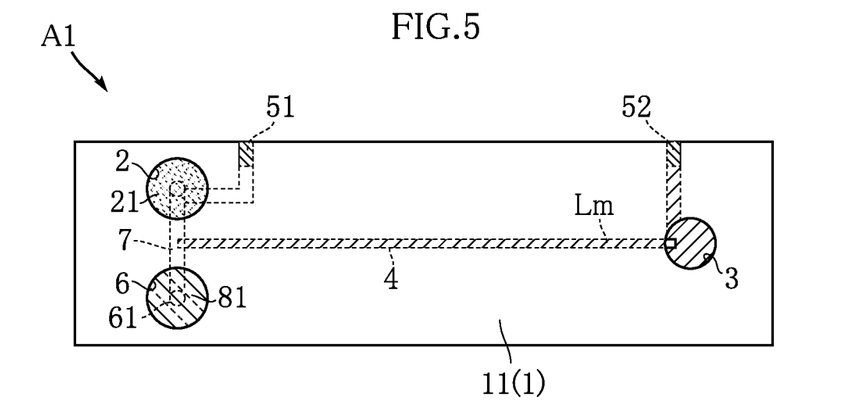
FIG. 5 is a plan view illustrating an analytical process using the analytical tool shown in FIG. 1.

Subsequently, the buffer solution Lm is introduced into the capillary tube 4. More specifically, as shown in FIG. 5, the buffer solution Lm is sucked from the buffer reservoir 992 into the inlet nozzle 94 and then introduced into the outlet reservoir 3. Then, pressure is appropriately applied to the outlet reservoir 3 by the pressure nozzle 96, causing the buffer solution Lm to flow into the capillary tube 4. Preferably, the buffer solution Lm also fills the electrode contact element 52.

<Mixing Step>

Figure 6:
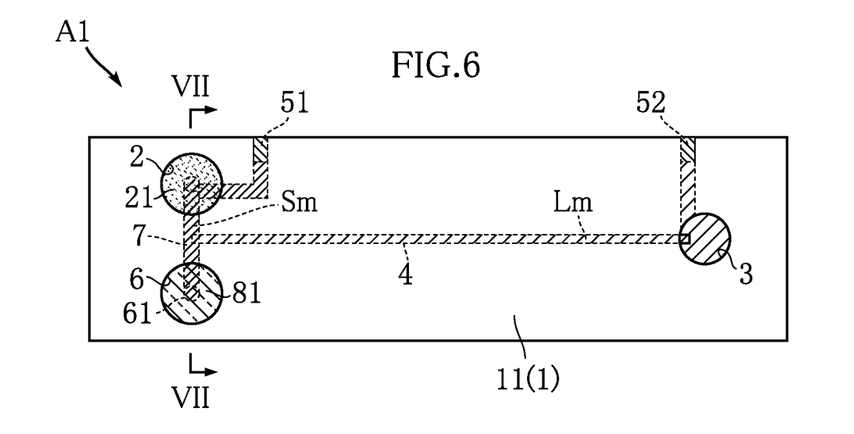
FIG. 6 is a plan view illustrating the analytical process using the analytical tool shown in FIG. 1.
Figure 7:
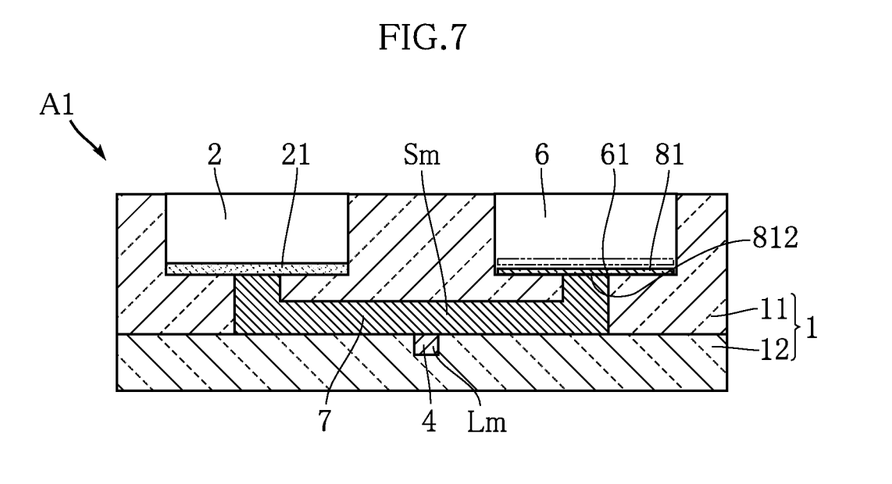
FIG. 7 is a cross-sectional view taken along line VII-VII of FIG. 6.

Subsequently, the sample is mixed with the diluent Ld. For example, the sample is dropped into the mixing reservoir, which is included in the analytical device or the analytical tool A1. The diluent Ld is sucked from the diluent reservoir 991 into the inlet nozzle 94 and then introduced into the mixing reservoir. As a result, the sample is diluted with the diluent Ld to prepare a diluted sample Sm. Note that experimental work by the inventors has found that one or more accessory ingredients (i.e., components other than the analyte components) of the blood sample may form aggregates with chondroitin sulfate (i.e., an example of the anionic group-containing compound) in the mixing step. The inventors have also identified lipids as specific examples of accessory ingredients that may form aggregates. The diluted sample Sm thus prepared is sucked into the inlet nozzle 94 and then introduced into the inlet reservoir 2 of the analytical tool A1. Then, pressure is applied to the inlet reservoir 2 by the pressure nozzle 95, causing the diluted sample Sm to flow into the connection channel 7 as shown in FIGS. 6 and 7. The diluted sample Sm passes through the filter 21 before flowing into the connection channel 7, so that aggregates of the accessory ingredients (such as lipids) and the anionic group-containing compound (chondroitin sulfate, in this embodiment) are removed by the filter 21 from the diluted sample Sm. The diluted sample Sm flows through the connection channel 7 to reach the secondary reservoir 6. Preferably, the diluted sample Sm also fills the electrode contact element 51.

<Electrophoresis Step>

Subsequently, the electrode 91 is brought into contact with the electrode contact element 51 and the electrode 92 with electrode contact element 52. Then, under control by the controller 98, a voltage of e.g., 0.5 to 20 kV is applied across the electrode contact elements 51 and 52 to induce an electroosmotic flow. As a result, the diluted sample Sm in the capillary tube 4 gradually moves with the electroosmotic flow. The light emitting unit 931 starts to emit light and the light receiving unit 932 measures the absorbance. Next, the absorbance is analyzed in relation to the time elapsed from the start of voltage application by the electrodes 91 and 92. Some components in the diluted sample Sm travel faster and thus exhibit an absorbance peak relatively short time after the start of voltage application. Some components in the diluted sample Sm travel slower and thus exhibit an absorbance peak relatively long time after the start of voltage application. This difference makes it possible to carry out analysis (separate measurement) of the individual components contained in the diluted sample Sm. The measured absorbance may be subjected to computation (such as differential or finite differences processing by the controller 98) to create an electropherogram. Calculating a peak height or a peak area in this electropherogram can determine the factors related to the diluted sample Sm, such as the component ratios. The sample (diluted sample Sm) is analyzed through the above steps.

At least in one of the mixing step and the electrophoresis step, there is a time at which the diluted sample Sm comes into contact with the flat member 81 as shown in FIG. 7. In this embodiment, when the diluted sample Sm flowing through the connection channel 7 reaches the enlarged portion 61, the diluted sample Sm comes into contact with the hydrophilic surface 812 of the flat member 81. Due to the hydrophilicity of the hydrophilic surface 812, the diluted sample Sm rapidly spreads over the entire hydrophilic surface 812. As mentioned above, the flat member 81 is simply placed on the bottom of the secondary reservoir 6. Therefore, in response to a pressure for further pushing the diluted sample Sm into the secondary reservoir 6, the flat member 81 is slightly lifted upward as seen in the figure, allowing some of the diluted sample Sm to enter the secondary reservoir 6.

In a specific analysis performed according to the present embodiment, the sample used in this embodiment was 1.5 µL of whole blood collected from a human body. The collected sample was diluted with 60 µL of the diluent Ld to prepare a diluted sample Sm. The diluent Ld was prepared by using 38 mM citric acid, 0.95% (w/v) chondroitin sulfate C-sodium, 475 mM of NDSB-201 (available from Anatrace), 19 mM of MES, 0.1% (w/v) of EMULGEN LS-110 (available from Kao Corporation), 0.02% (w/v) of sodium azide, and 0.025% (w/v) ProClin™ 950 (available from Sigma-Aldrich), followed by pH adjustment to pH 6.0 using dimethylaminoethanol (for pH adjustment). The buffer solution Lm was prepared by using 40 mM of citric acid, 1.25% (w/v) chondroitin sulfate C-sodium, 20 mM of piperazine, 0.1% (w/v) of EMULGEN LS-110 (available from Kao Corporation), 0.02% (w/v) of sodium azide, and 0.025% (w/v) ProClin™ 950 (available from Sigma-Aldrich), followed by pH adjustment to pH 5.0 using dimethylaminoethanol (for pH adjustment). The light receiving unit 932 measured the absorbance at 415 nm. The duration of electrophoresis was 35 seconds.

The following now describes the operations of the analytical tool A1 and the analytical system C.

Figure 9:
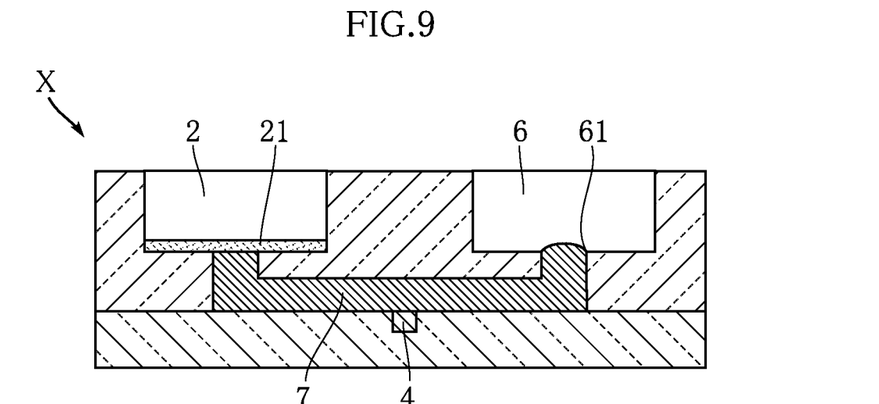
FIG. 9 is a cross-sectional view illustrating an analytical process using an analytical tool of a comparative example.

According to this embodiment, the diluted sample Sm reaching the enlarged portion 61 comes into contact with the flat member 81, which acts as a pressure fluctuation reducer. For the purpose comparison, an analytical tool X of a comparative example is discussed. As shown in FIG. 9, the analytical tool X is not provided with the flat member 81. Therefore, a diluted sample Sm reaching the enlarged portion 61 will have a top surface assuming a shape that bulges upward into the secondary reservoir 6. This bulging shape of the diluted sample Sm tends to deform frequently depending, for example, on the pressure applied to the diluted sample Sm. In addition, the diluted sample Sm cannot freely flow back into the inlet reservoir 2 as the inlet reservoir 2 is closed by the filter 21 used to remove interfering substances from the diluted sample Sm. Thus, a change in the bulging shape of the diluted sample Sm at the enlarged portion 61 directly causes a pressure change across the diluted sample Sm. Such a pressure change may cause unintentional migration of the buffer solution Lm and the diluted sample Sm in the capillary tube 4. Such a pressure change is especially detrimental during the electrophoresis step because the analyte components in the diluted sample Sm may be induced to migrate independently of the migration by electrophoresis. In this embodiment, however, the flat member 81 prevents the diluted sample Sm from assuming the bulging shape, which tends to be easily deformed due to various factors. This configuration is effective to inhibit unintentional migration of the buffer solution Lm and the diluted sample Sm in the capillary tube 4. This embodiment therefore ensures appropriate removable of interfering substances as well as more proper analysis.

Figure 8:
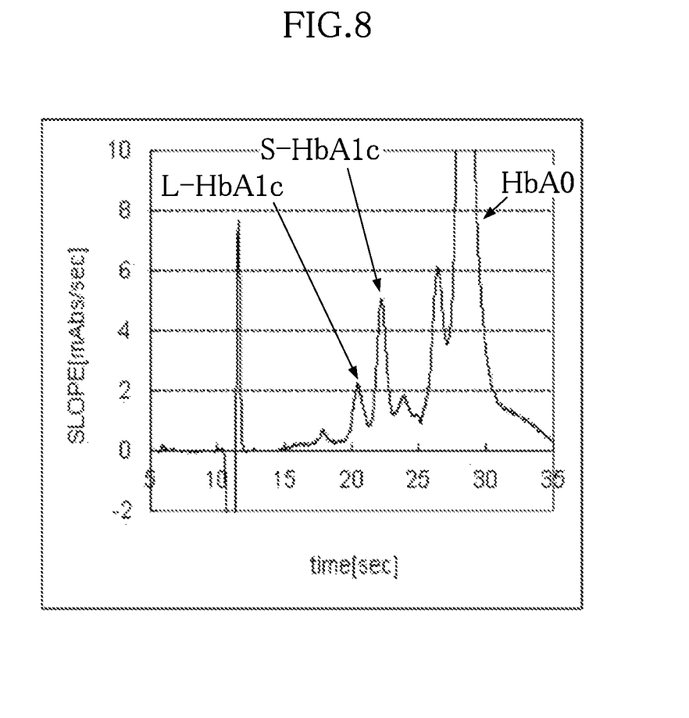
FIG. 8 is a graph showing exemplary analytical result obtained by the analytical process using the analytical tool shown in FIG. 1.
Figure 10:
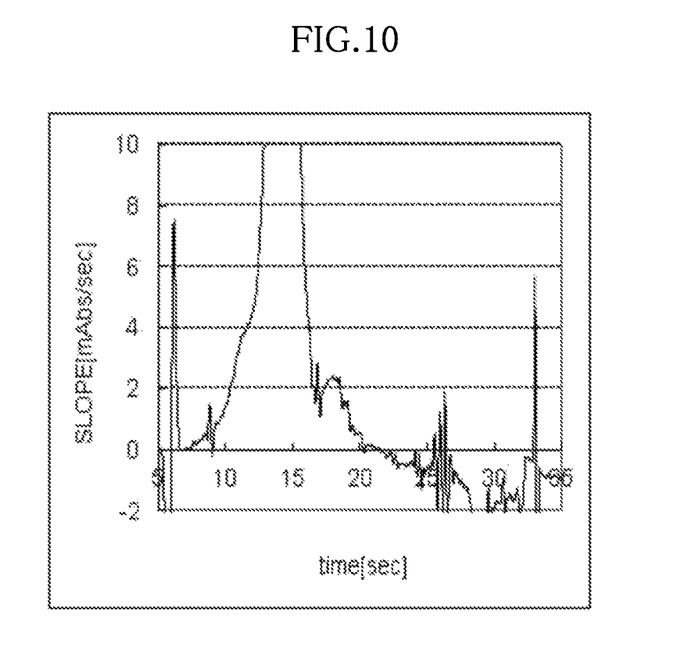
FIG. 10 is a graph showing exemplary analytical result obtained by the analytical process using the analytical tool of the comparative example.
Figure 11:
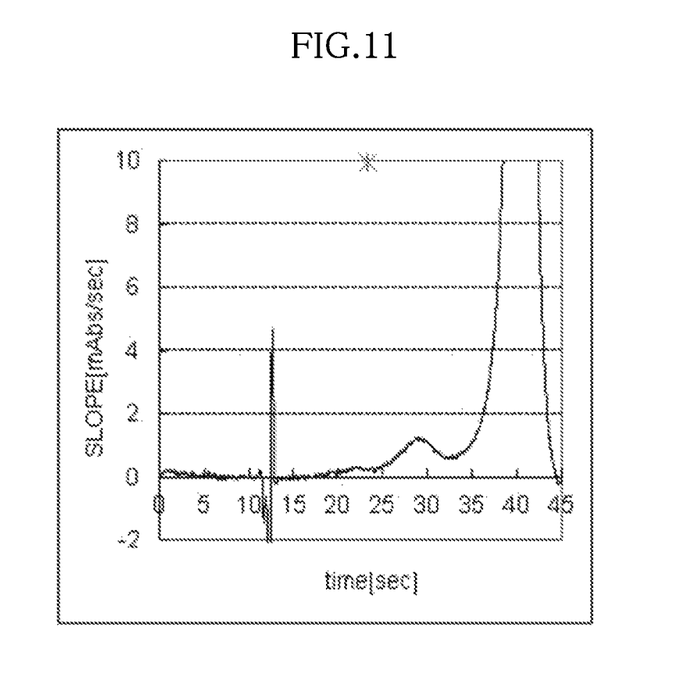
FIG. 11 is a graph showing exemplary analytical result obtained by another analytical process using the analytical tool of the comparative example.

FIG. 8 is a graph showing the analytical result obtained by the analytical process according to this embodiment. The horizontal axis represents the time of measurement, whereas the vertical axis represents the absorbance change rate. As can be seen, the graph of this embodiment shows clear peaks corresponding to the analyte components, namely L-HbA1c, S-HbA1c and HbA0. FIGS. 10 and 11 are graphs showing the analytical result obtained by using the analytical tool X of the comparative example shown in FIG. 9. More specifically, FIG. 10 shows the analytical result obtained by introducing the diluted sample Sm until it flows out of the secondary reservoir 6, whereas FIG. 11 shows the analytical result obtained by introducing the diluted sample Sm so as not to reach the opening of the secondary reservoir 6 or the enlarged portion 61. Unlike the graph of FIG. 8, the graphs of the comparative examples show no clear peaks corresponding to the analyte components. The absence of clear peaks is due to unintentional migration of the buffer solution Lm and the diluted sample Sm in the capillary tube 4, and the unintentional migration is caused by the pressure fluctuations resulting from the surface tension of the diluted sample Sm.

The flat member 81 is made from a resin impermeable to the diluted sample Sm and simply placed on the bottom of the secondary reservoir 6. Therefore, the flat member 81 prevents the diluted sample Sm from forming a bulging surface shape at the enlarged portion 61, while allowing the diluted sample Sm to flow into the secondary reservoir 6 in response to a pressure pushing the diluted sample Sm. This configuration is preferable to avoid excessive fluctuations of the pressure acting on the diluted sample Sm.

In addition, the flat member 81 has the hydrophilic surface 812 facing the enlarged portion 61. Therefore, the diluted sample promptly spreads over the entire hydrophilic surface 812 upon reaching the enlarged portion 61. This configuration is effective to prevent the diluted sample Sm from forming a bulging surface shape by the action of surface tension.

FIGS. 12 to 24 show other embodiments of the present invention. In these figures, elements identical or similar to those of the foregoing embodiment are designated by the same reference signs as those used for the foregoing embodiment.

Figure 12:
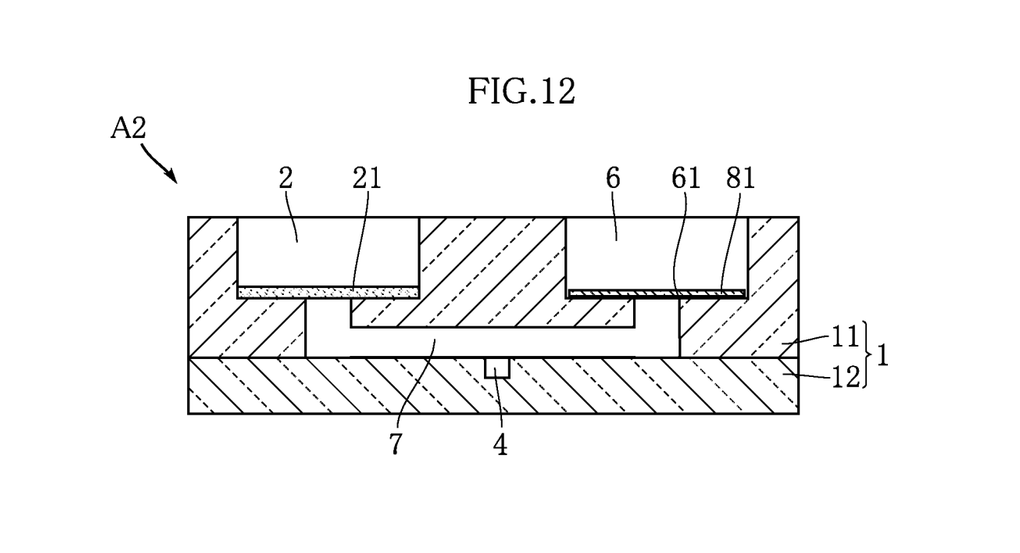
FIG. 12 is a cross-sectional view showing an analytical tool according to Embodiment 2 of the present invention.
Figure 13:
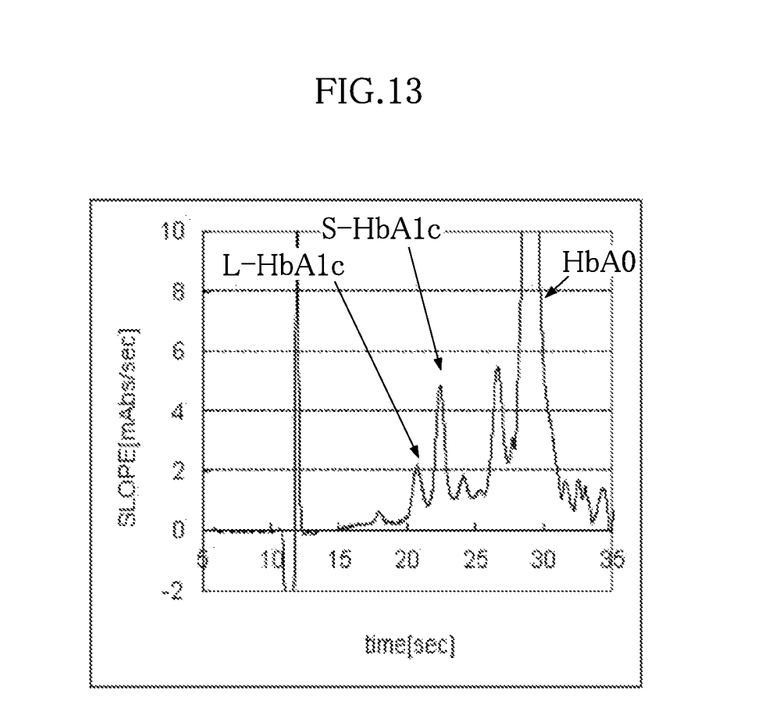
FIG. 13 is a graph showing exemplary analytical result obtained by an analytical process using the analytical tool shown in FIG. 12.

FIG. 12 shows an analytical tool according to Embodiment 2 of the present invention. The analytical tool A2 of this embodiment differs from the analytical tool A1 in that the flat member 81 does not have a hydrophilic surface 812 facing the enlarged portion 61. FIG. 13 is a graph showing the analytical result obtained by an analytical process using the analytical tool A2. Other than the configuration of the flat member 81, the analytical process of this embodiment is performed under the same conditions as the analytical process performed using the analytical tool A1. The graph of this embodiment shows clear peaks corresponding to the analyte components, indicating that the flat member 81 of this embodiment is effective to substantially reduce pressure fluctuations caused by the surface tension.

Figure 14:
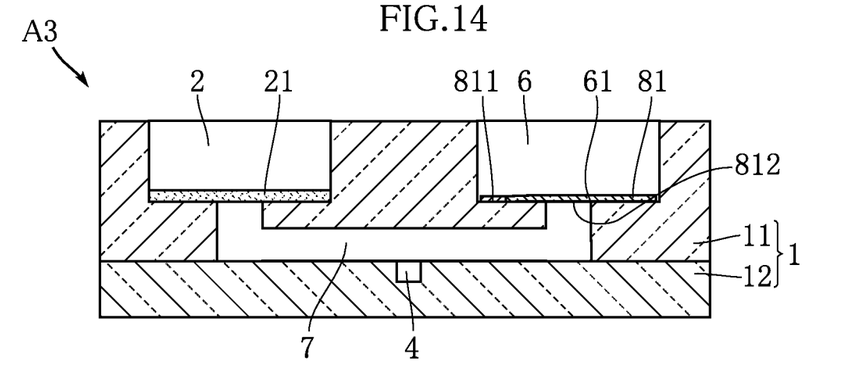
FIG. 14 is a cross-sectional view showing an analytical tool according to Embodiment 3 of the present invention.

FIG. 14 shows an analytical tool according to Embodiment 3 of the present invention. The analytical tool A3 of this embodiment differs from the analytical tools A1 and A2 described above in that the flat member 81 has a portion 811 fixed to the secondary reservoir 6. The fixed portion 811 is a portion of the flat member 81 secured to the bottom of the secondary reservoir 6 by heat fusing or adhesive. This configuration enables the flat member 81 to act as a value. This embodiment is effective to substantially reduce pressure fluctuations caused by the surface tension of the diluted sample Sm at the enlarged portion 61.

Figure 15:
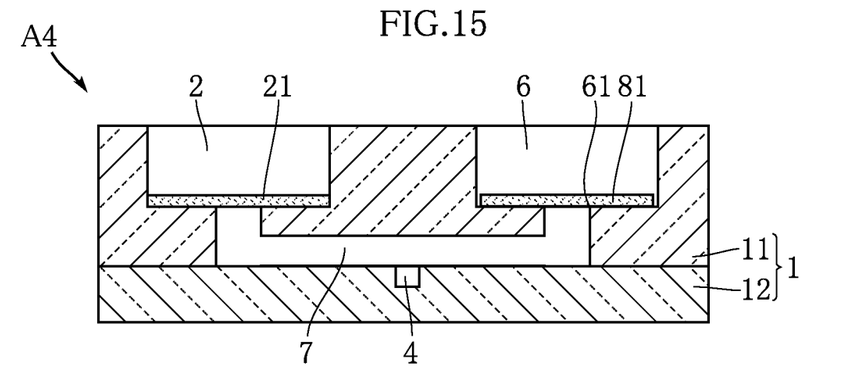
FIG. 15 is a cross-sectional view showing an analytical tool according to Embodiment 4 of the present invention.

FIG. 15 shows an analytical tool according to Embodiment 4 of the present invention. The analytical tool A4 of this embodiment differs from the foregoing embodiments in that the flat member 81, as well as the filter 21, is made of a porous medium that allows a liquid to pass through. Specific examples of porous mediums usable for the flat member 81 are the same as those for the filter 21. The flat member 81 of this embodiment is placed on the bottom of the secondary reservoir 6 without being fixed.

Figure 16:
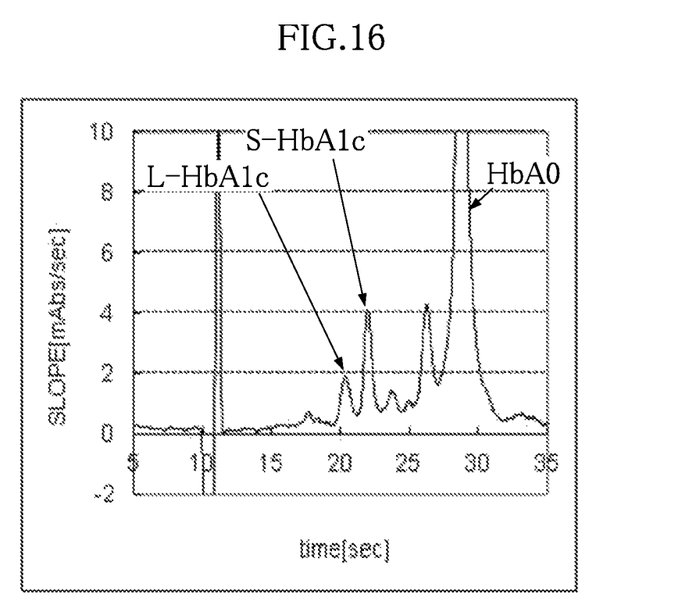
FIG. 16 is a graph showing exemplary analytical result obtained by an analytical process using the analytical tool shown in FIG. 15.

FIG. 16 is a graph showing the analytical result obtained by an analytical process using the analytical tool A4. Other than the configuration of the flat member 81, the analytical process of Embodiment 2 is performed under the same conditions as the analytical process performed using the analytical tool A1. The graph of this embodiment shows clear peaks corresponding to the analyte components, indicating that the flat member 81 made of a porous medium is effective to substantially reduce pressure fluctuations caused by the surface tension.

Figure 17:
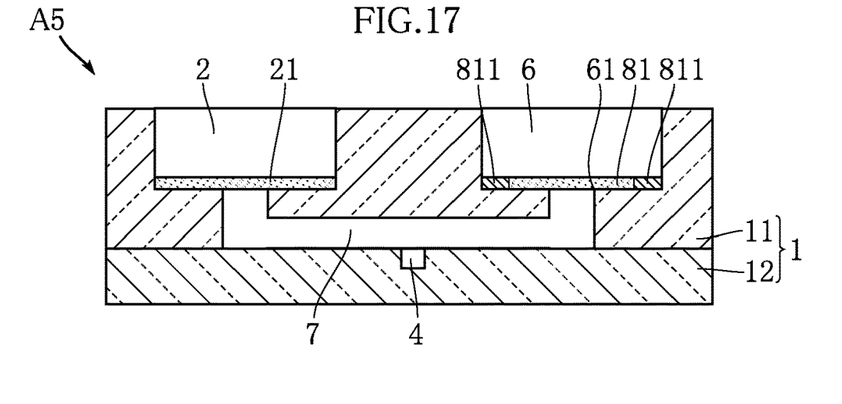
FIG. 17 is a cross-sectional view showing an analytical tool according to Embodiment 5 of the present invention.

FIG. 17 shows an analytical tool according to Embodiment 5 of the present invention. The analytical tool A5 of the present invention is similar to the analytical tool A4 in that the flat member 81 is made of the same porous medium as the filter 21. The difference lies in that the flat member 81 of this embodiment has a portion 811 fixed to the bottom of the secondary reservoir 6. In this embodiment, the fixed portion 811 may extend along the entire outer edge of the flat member 81 and still allows a liquid to pass through owing to the flat member 81 being porous.

Figure 18:
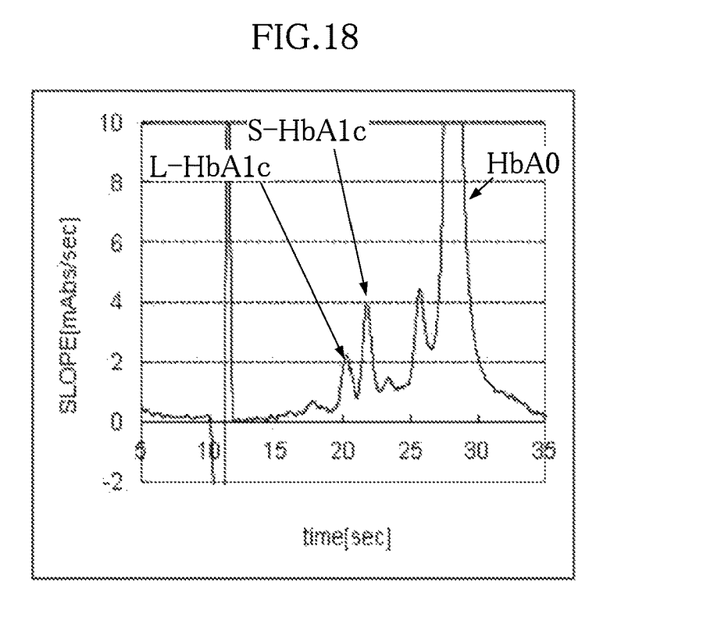
FIG. 18 is a graph showing exemplary analytical result obtained by an analytical process using the analytical tool shown in FIG. 17.

FIG. 18 is a graph showing the analytical result obtained by an analytical process using the analytical tool A5. Other than the configuration of the flat member 81, the analytical process of Embodiment 5 is performed under the same conditions as the analytical process performed using the analytical tool A1. The graph of this embodiment shows clear peaks corresponding to the analyte components, indicating that the porous flat member 81 having the fixed portion 811 is effective to substantially reduce pressure fluctuations caused by the surface tension.

Figure 19:
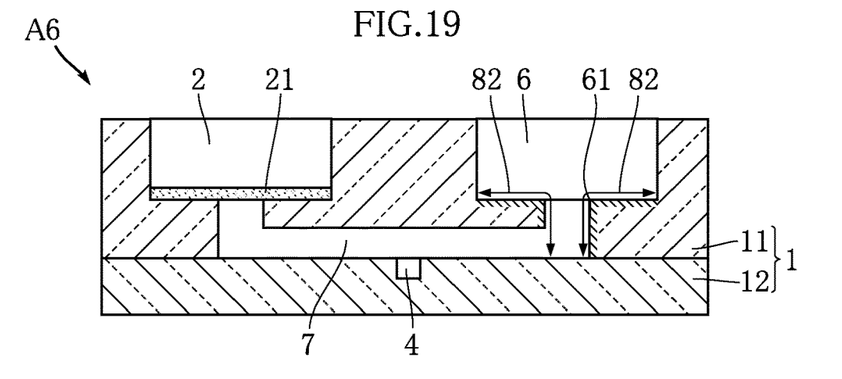
FIG. 19 is a cross-sectional view showing an analytical tool according to Embodiment 6 of the present invention.

FIG. 19 shows an analytical tool according to Embodiment 6 of the present invention. The analytical tool A6 of this embodiment differs in that the enlarged portion 61 has an inner surface that includes a hydrophilic region 82. The hydrophilic region 82 is an inner surface area of the enlarged portion 61 treated to be hydrophilic. This embodiment having such a configuration ensures that the diluted sample Sm reaching the enlarged portion 61 promptly spreads over the hydrophilic region 82. Consequently, the diluted sample Sm does not form a bulging shape on the top surface reaching the enlarged portion 61. This embodiment is effective to substantially reduce pressure fluctuations caused by the surface tension of the diluted sample Sm.

Figure 20:
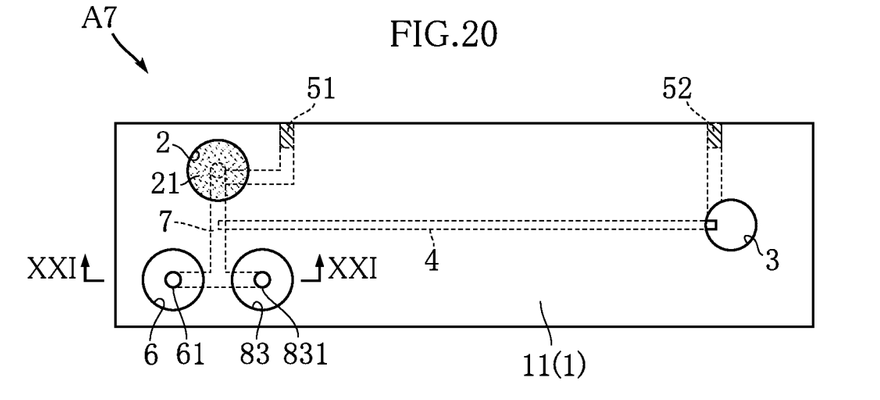
FIG. 20 is a cross-sectional view showing an analytical tool according to Embodiment 7 of the present invention.
Figure 21:
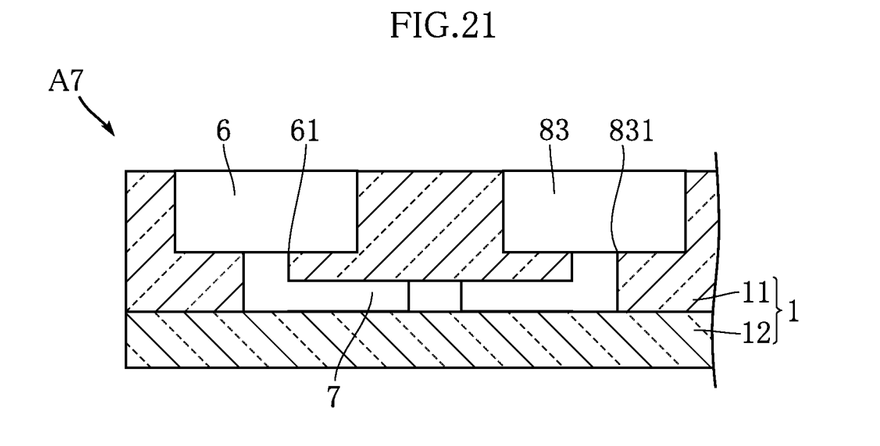
FIG. 21 is a cross-sectional view taken along line XXI-XXI of FIG. 20.

FIGS. 20 and 21 each show an analytical tool according to Embodiment 7 of the present invention. This embodiment differs from the foregoing embodiments in that the analytical tool A7 additionally includes an open reservoir 83, which is one example of the pressure fluctuation reducer. The open reservoir 83 is a separate reservoir from the secondary reservoir 6 and is in communication with the secondary reservoir 6 through the connection channel 7. The open reservoir 83 is open at the top as shown in FIG. 21. The open reservoir 83 shown in FIGS. 20 and 21 is similar in shape to the secondary reservoir 6 and has an enlarged portion 831.

In this embodiment, when a pressure is applied to the diluted sample Sm in response to the surface tension fluctuations at the enlarged portion 61, the pressure is released from the open reservoir 83 that is open to the atmosphere. Therefore, the pressure fluctuations caused by the surface tension does not affect the buffer solution Lm and the diluted sample Sm in the capillary tube 4. This configuration ensures appropriate removable of interfering substances as well as more reliable analysis. Note that the surface tension fluctuations may occur at the enlarged portion 831. In this case, the pressure is released from the secondary reservoir 6. In this way, the secondary reservoir 6 and the open reservoir 83 have similar functions.

Figure 22:
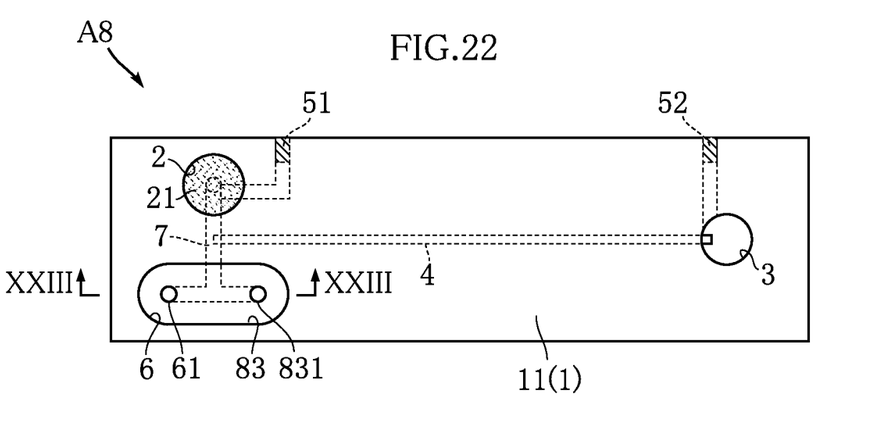
FIG. 22 is a plan view showing an analytical tool according to Embodiment 8 of the present invention.
Figure 23:
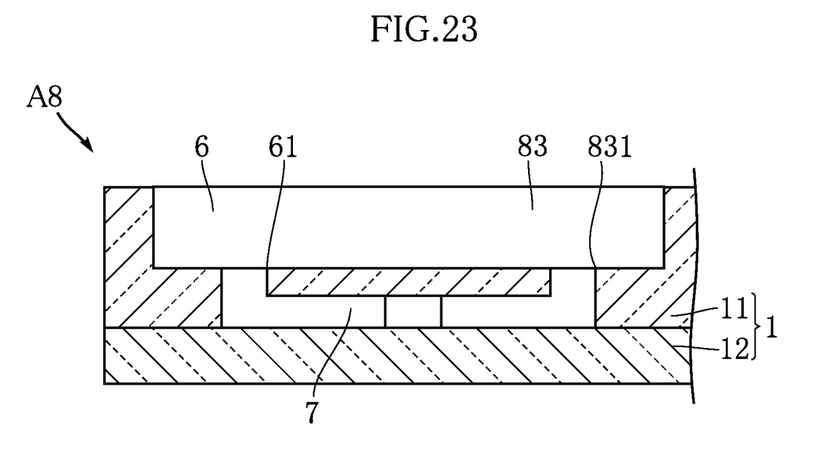
FIG. 23 is a cross-sectional view taken along line XXIII-XXIII of FIG. 22.

FIGS. 22 and 23 each show an analytical tool according to Embodiment 8 of the present invention. The analytical tool A8 of this embodiment has an open reservoir 83 that is continuous with the secondary reservoir 6. In other words, the secondary reservoir 6 and the open reservoir 83 together form one reservoir that is open at the top as seen in FIG. 23. This configuration ensures appropriate removable of interfering substances as well as more reliable analysis.

Figure 24:
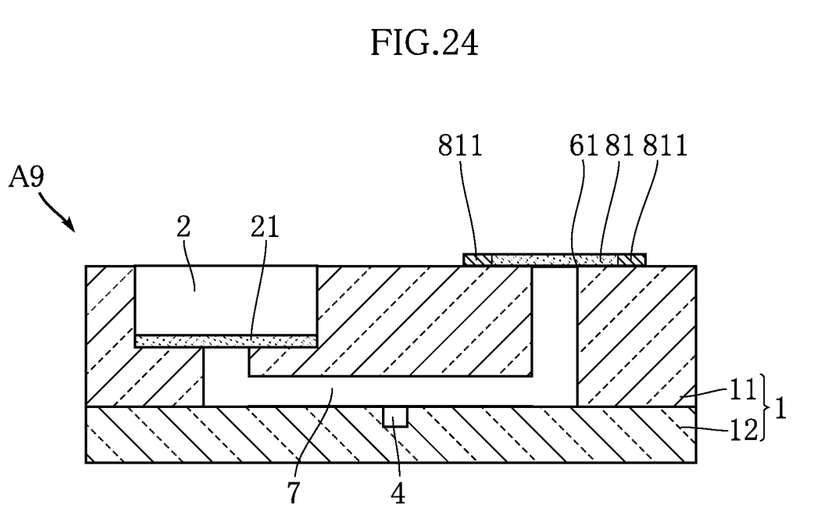
FIG. 24 is a cross-sectional view showing an analytical tool according to Embodiment 9 of the present invention.

FIG. 24 shows an analytical tool according to Embodiment 9 of the present invention. The analytical tool A9 of this embodiment differs from the foregoing embodiments in that the secondary reservoir 6 is not provided. The enlarged portion 61 of this embodiment corresponds to where the connection channel 7 opens in the outer surface of the body 1. The analytical tool A9 has a flat member 81 that is one example of the pressure fluctuation reducer. This flat member 81 has a portion 811 is fixed to the enlarged portion 61. In addition, this flat member 81, as well as e.g., the filter 21, is made of a porous medium allowing a liquid to pass through. The pressure fluctuation reducer of this embodiment may be combined with any configuration described in the foregoing embodiments. This embodiment ensures appropriate removable of interfering substances as well as more reliable analysis.

The analytical tool and the analytical system according to the present invention are not limited to the foregoing embodiments. Various design changes can be made to the specific configurations of the constituent parts of the analytical tool and the analytical system according to the present invention.

The invention claimed is:

1. An analytical tool for analysis of a sample by capillary electrophoresis, comprising:
   an inlet reservoir into which a sample is introduced;
   a secondary reservoir having an opening at a bottom of the secondary reservoir;
   a connection channel connecting the inlet reservoir to the bottom of the secondary reservoir through the opening, wherein the sample is introduced from the inlet reservoir into the secondary reservoir through the connection channel and the opening of the bottom of the secondary reservoir, an area of the bottom being larger than the cross-section area of the connection channel;
   a flat member which is liftably placed on the bottom of the secondary reservoir so as to cover the opening of the secondary reservoir, contacts with the sample reaching to the secondary reservoir, and allows the sample in the connection channel to enter the secondary reservoir when the flat member is lifted, wherein the flat member is not fixed to the secondary reservoir; and
   a capillary tube in communication with the connection channel at a location between the inlet reservoir and the secondary reservoir, wherein a voltage is applied to the capillary tube for causing electrophoresis.

2. The analytical tool according to claim 1, wherein the flat member is made of a liquid-impermeable resin.

3. The analytical tool according to claim 1, wherein the flat member has a hydrophilic surface facing the bottom of the secondary reservoir.

4. The analytical tool according to claim 1, wherein the analytical tool is configured as a disposable tool.

5. The analytical tool according to claim 1, further comprising an analyzing unit into which the analytical tool is installed and configured to perform analysis by capillary electrophoresis in the capillary tube.

6. An analytical tool for analysis of a sample by capillary electrophoresis, comprising:
   an inlet reservoir into which a sample is introduced;
   a secondary reservoir having an opening at a bottom of the secondary reservoir;
   a connection channel connecting the inlet reservoir to the bottom of the secondary reservoir through the opening, wherein the sample is introduced from the inlet reservoir into the secondary reservoir through the connection channel and the opening of the bottom of the secondary reservoir, an area of the bottom being larger than the cross-section area of the connection channel;
   a flat member which is liftably placed on the bottom of the secondary reservoir so as to cover the opening of the secondary reservoir, contacts with the sample reaching to the secondary reservoir, and allows the sample in the connection channel to enter the secondary reservoir when the flat member is lifted, wherein the flat member is not fixed to the secondary reservoir; and
   a capillary tube in communication with the connection channel at a location between the inlet reservoir and the secondary reservoir, wherein the flat member has a hydrophilic surface facing the bottom of the secondary reservoir.

7. The analytical tool according to claim 6, wherein the flat member is made of a liquid-impermeable resin.

8. The analytical tool according to claim 6, wherein the analytical tool is configured as a disposable tool.

9. The analytical tool according to claim 6, further comprising an analyzing unit into which the analytical tool is installed and configured to perform analysis by capillary electrophoresis in the capillary tube.

10. The analytical tool according to claim 1, wherein the flat member is entirely liftable.

11. The analytical tool according to claim 6, wherein the flat member is entirely liftable.

12. An analytical tool for analysis of a sample by capillary electrophoresis, comprising:
    an inlet reservoir into which a sample is introduced;
    a secondary reservoir having an opening at a bottom of the secondary reservoir;
    a connection channel connecting the inlet reservoir to the bottom of the secondary reservoir through the opening, wherein the sample is introduced from the inlet reservoir into the secondary reservoir through the connection channel and the opening of the bottom of the secondary reservoir, an area of the bottom being larger than the cross-section area of the connection channel;
    a flat member which is liftably placed on the bottom of the secondary reservoir so as to cover the opening of the secondary reservoir, contacts with the sample reaching to the secondary reservoir, and allows the sample in the connection channel to enter the secondary reservoir when the flat member is lifted, wherein the flat member is entirely liftable; and
    a capillary tube in communication with the connection channel at a location between the inlet reservoir and the secondary reservoir, wherein a voltage is applied to the capillary tube for causing electrophoresis.

* * * * *